United States Patent [19]
Ko

[11] Patent Number: 4,819,648
[45] Date of Patent: * Apr. 11, 1989

[54] NON-INVASIVE ELECTROMAGNETIC TECHNIQUE FOR MONITORING TIME-TRENDS OF PHYSIOLOGICAL CHANGES AT A PARTICULAR LOCATION IN THE BRAIN

[75] Inventor: Harvey W. Ko, Columbia, Md.

[73] Assignee: The Johns Hopkins University, Baltimore, Md.

[*] Notice: The portion of the term of this patent subsequent to Sep. 1, 2004 has been disclaimed.

[21] Appl. No.: 92,268

[22] Filed: Sep. 1, 1987

Related U.S. Application Data

[63] Continuation-in-part of Ser. No. 791,864, Oct. 28, 1985, Pat. No. 4,690,149.

[51] Int. Cl.⁴ .................................................. A61B 5/05
[52] U.S. Cl. ..................................... 128/653; 128/234; 324/202; 324/236
[58] Field of Search ............... 128/734, 630, 774, 748, 128/653, 1.3–1.5; 324/202, 236, 237

[56] References Cited

U.S. PATENT DOCUMENTS

| 3,723,861 | 3/1973 | Samples | 324/237 |
| 4,458,202 | 7/1984 | Nefedov et al. | 324/236 |
| 4,564,810 | 1/1986 | Geithman et al. | 324/236 |
| 4,690,149 | 9/1987 | Ko | 128/734 |
| 4,721,113 | 1/1988 | Stewart et al. | 128/661 |

Primary Examiner—Ruth S. Smith
Attorney, Agent, or Firm—Robert E. Archibald; Howard W. Califano

[57] ABSTRACT

An apparatus and method for non-invasively sensing physiological changes in the brain is disclosed. The apparatus and method uses an electromagnetic field to measure localized impedance changes in brain matter and fluid. The apparatus and method has particular application in providing time-trend measurements of the process of brain edema associated with head trauma.

9 Claims, 3 Drawing Sheets

|  |  | TEMPERATURE (°C) | | | |
| --- | --- | --- | --- | --- | --- |
|  |  | 12 | 13 | 20 | |
| WHITE | NORMAL | 0.15 ± 0.03 | 0.15 ± 0.01 | 0.14 ± 0.02 | CONDUCTIVITY IN mho/METER |
|  | EDEMATOUS | 0.16 ± 0.01 | 0.18 ± 0.01 | 0.18 ± 0.01 | |
| GREY | NORMAL | 0.20 ± 0.01 | 0.21 ± 0.02 | 0.12 ± 0.02 | |
|  | EDEMATOUS | 0.38 ± 0.04 | 0.30 ± 0.07 | 0.36 ± 0.07 | |
*FIG. 1*
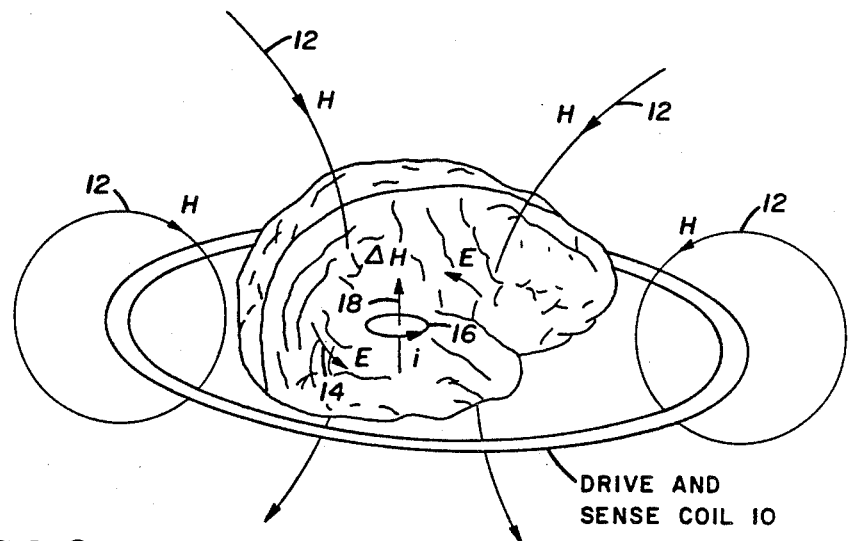
*FIG. 2*
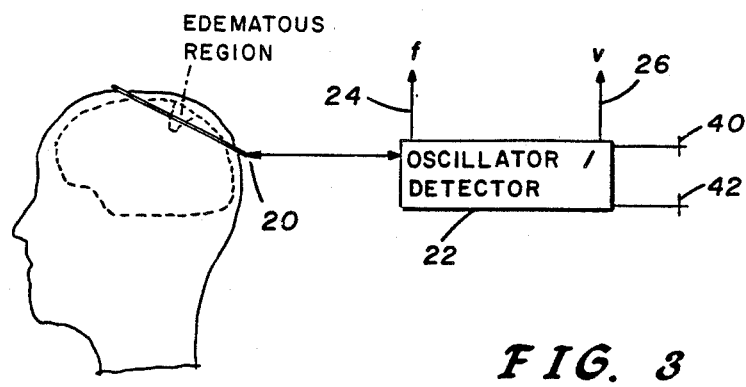
*FIG. 3*

NON-INVASIVE ELECTROMAGNETIC TECHNIQUE FOR MONITORING TIME-TRENDS OF PHYSIOLOGICAL CHANGES AT A PARTICULAR LOCATION IN THE BRAIN

STATEMENT OF GOVERNMENTAL INTEREST

The Government has rights in this invention pursuant to Contract No. N00039-87-C-5301 (formerly N00024-85-C-5301), awarded by the Department of the Navy.

REFERENCE TO RELATED CASES

This is a continuation-in-part of a patent application filed on Oct. 28, 1985, Ser. No. 791,864 (now U.S. Pat. No. 4,690,149).

BACKGROUND OF THE INVENTION

1. Field of the Invention

The invention relates to a method and apparatus for using an electromagnetic technique to monitor physiological changes in the brain. More particularly, the invention uses an electromagnetic field to non-invasively measure impedance changes at a localized point within an animal or human brain over time. For example, these localized impedance measurements can be used to detect and monitor the advent and growth of edematous tissue, or the process of hydrocephalus.

2. Description of the Prior art

It is important in diagnosing and treating various life-threatening conditions, such as brain edema and hydrocephalus, to monitor the time-trends of physiological changes in the brain. Brain edema, which is an increase in brain volume caused by grey and/or white brain tissue absorbing edematous fluid, can develop from general hypoxia; from cerebral hemorrhage, thrombosis, or embolus; from trauma (including post-surgical); from a tumor; or from inflammatory diseases of the brain. Brain edema can directly compromise vital functions, distort adjacent structures, or interfere with perfusion. It can produce injury indirectly by increasing intracranial pressure. In short, brain edema is often a life-threatening manifestation of a number of disease processes.

There are several effective therapeutic measures to treat brain edema. These include osmotic agents, corticosteroids, hyperventilation to produce hypocapnia, and surgical decompression. As with all potent therapy, it is important to have a continuous measure of its effect on the manifestation, in this case, the brain edema.

All current techniques for measuring physiological changes in the brain, including the manifestation of brain edema, have shortcomings in providing continuous or time-trend measurements. Intracranial pressure can be monitored continuously, but this is an invasive procedure. Furthermore, intracranial compliance is such that substantial edema must occur before there is any significant elevation in pressure. When the cranium is disrupted surgically or by trauma, or is compliant (as in infants), the pressure rise may be further delayed. These patients are often comatose, and localizing neurological signs are a late manifestation of edema. Impairment of respiration and circulation are grave late signs. Thus, clinical examination is not a sensitive indicator of the extent of edema. X-ray computed tomography (CT) scanning can produce valuable evidence of structural shifts produced by brain edema, and it is a non-invasive procedure. Structural shirts, however, may not correlate well with dysfunction, especially with diffuse edema. Furthermore, frequent repetition is not feasible, particularly with acutely ill patients. NMR proton imaging can reveal changes in brain water, it does not involve ionizing radiation, and it is non-invasive. However, it does not lend itself to frequent repetition in the acutely ill patient. PET scanning can reveal the metabolic disturbances associated with edema and will be invaluable in correlating edema with its metabolic consequences. However, it too is not suited to frequent repetition.

For these reasons it would be a significant advance to have a measurement which (1) gives reliable time-trend information continuously; (2) is non-invasive; (3) does not depend upon the appearance of increased intracranial pressure, and (4) can be performed at the bedside even in the presence of life-support systems.

As will be discussesd in detail subsequently in this application, Applicant has related localized impedance changes in the brain with physiological changes in the brain. Applicant was the first to identify that edematous tissue has a significantly different conductivity from healthy white or grey matter.

To non-invasively detect such an impedance change, Applicant has invented a method and apparatus which uses an electromagnetic field for sensing such an impedance change at localized portions of the brain. U.S. Pat. No. 3,735,245 entitled "Method and Apparatus for Measuring Fat Content in Animal Tissue Either in Vivo or in Slaughtered and Prepared Form", invented by Wesley H. Harker, teaches that the fat content in meat can be determined by measuring the impedance difference between fat and meat tissue. The Harker apparatus determines gross impedance change and does not provide adequate spatial resolution for the present use. As will be discussed in detail later, brain impedance measurements must be spatially localized to provide a useful measure of physiological changes. A general measurement of intracranial conductivity would not be revealing, since as in the case of brain edema, the edematous fluid would initially displace CSF fluid and blood from the cranium; and, since these fluids have similar conductivities, a condition of brain edema would be masked.

U.S. Pat. No. 4,240,445 invented by Iskander et al teaches the use of an electromagnetic field responsive to the dielectric impedance of water to detect the presence of water in a patient's lung. The Iskander et al apparatus generates an electromagnetic wave using a microwave strip line. Impedance changes within the skin depth of the signal will cause a mode change in the propagating wave which is detected by associated apparatus. Therefore, Iskander et al uses a different technique from the present invention and does not detect conductivity variations with the degree of localization required in the present invention. U.S. Pat. No. 3,789,834, invented by Duroux, relates to the measurement of body impedance by using a transmitter and receiver and computing transmitted wave impedance from a propagating electromagnetic field. The Duroux apparatus measures passive impedance along the path of the propagating wave, whereas the present invention measures localized impedance changes in brain matter and fluid by measuring the eddy currents generated in localized portions of the brain matter and fluid. None of the above-cited references contemplate measuring localized impedance changes in the brain to evaluate physiological changes in the brain, such as the occurrence of edematous tissue, and none of the references teach an apparatus capable of such spatially localized impedance measurements.

SUMMARY OF THE INVENTION

Applicant was the first to discover that edematous tissue has a significantly different conductivity (or impedance) from normal white or grey brain matter. Applicant believes that edematous tissue is formed when white or grey matter in the brain becomes diffused or prefused with edematous fluid by an as yet unknown intercellular or extracellular process. As will be described later, the discovery that impedance changes can be used to identify edematous tissue was made using invasive probes. Applicant generally found that the conductivity change between normal and edematous grey tissue, for instance, would change by as much as 0.14 mho/meter, or equivalently by 100% of the normal value.

The present invention detects the increase in conductivity (or decrease in impedance) of brain tissue overtime to identify edematous tissue in an area of the brain. Edematous tissue may occur in localized areas near the surface of the cranium or may occur deeper in the brain. Since edematous tissue swells, blood and CSF fluid in the brain which may have the same conductivity as edema fluid, might be displaced. Therefore, localized spatially discrete changes in impedance over time must be measured to detect the physiological changes associated with brain edema at a particular location in the brain.

Further, monitoring localized impedance changes in the brain will allow one to measure and diagnose hydrocephalus since an increase in the ventricular volume will result in an increase in conductivity in certain localized areas of the brain. This is because CSF fluid which fills the expanded ventricle has a significantly greater conductivity (1.5–1.75 mho/meter) than white matter (0.10 to 0.15 mho/meter) or grey matter (0.12 to 0.23 mho/meter).

Applicant also realized that such localized impedance changes can be sensed non-invasively using a magnetic field and detecting the changes in mutual inductance between the brain and a sense coil. The apparatus described herein, and also described in part in a copending commonly assigned patent applications entitled "Electromagnetic Bone Healing Sensor" (U.S. Pat. No. 4,688,580), and "Non-invasive Electromagnetic Technique for Monitoring Physiological Changes in the Brain" (U.S. Pat. No. 4,690,149), generates a spatially discrete oscillating magnetic field which radiates a preselected location of the brain. The magnetic field induces eddy currents in brain tissue and fluid in the radiated area. When these eddy current are generated, they produce a secondary weak magnetic field which is detected by the apparatus. The magnitude of the eddy currents is proportional to the actual impedance of the tissue and fluid where the eddy currents are generated. The magnitude of the eddy currents in turn directly affect the magnitude of the secondary weak magnetic field.

The invented apparatus is capable of detecting small variations in impedance changes and quantitatively measuring such changes. A magnetic drive/sensor means is designed to concentrate the magnetic field in spatially localized areas within the brain. The invention also teaches various techniques for monitoring a preselected and localized area in the brain over time to generate a time-trend view of brain impedance. An oscillator detector in combination with the magnetic drive/sensor means is specially designed to be sensitive to small impedance changes and to reduce polarization effects and background noise which could render such monitoring impossible.

It is hoped that continuous monitoring of a patient at his bedside would enable physicians to treat the first sign of swelling and also to measure any therapy's effectiveness. The invented device may prevent much of the brain damage that results from head injuries, stroke, brain tumors or drug abuse when injured brain tissue swells and presses against the inside of the skull.

BRIEF DESCRIPTION OF THE DRAWINGS

FIG. 1 is a table showing the difference in conductivity between normal and edematous white and grey matter found in a rabbit brain.

FIG. 2 is a graphic representation of the invented non-invasive principal for measuring brain impedance.

FIG. 3 is a block diagrammatic illustration of the present invention showing the use of a drive/sensor loop coil.

DETAILED DESCRIPTION OF THE PREFERRED EMBODIMENT

Figure 4:
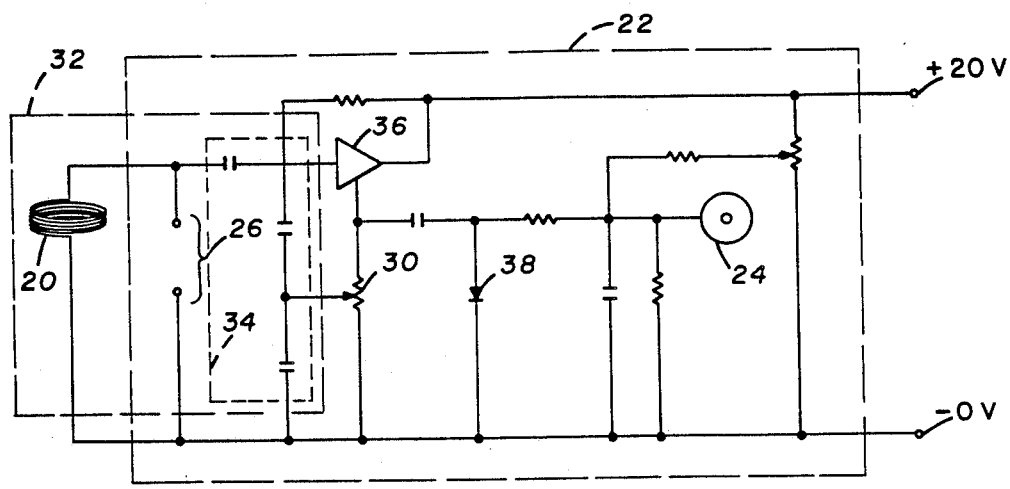
FIG. 4 is a schematic diagram of a typical oscillator/detector circuit used in the present invention.

The present invention provides a method and apparatus for making continuous or time-trend measurements of the migration of CSF and edema fluid within brain tissue and of changes in biological substances in the brain. These biological changes within the brain are monitored by observing changes in local conductivity or impedance within the brain.

Applicant was the first to discover that edematous tissue has a significantly different conductivity (or impedance) from normal white or grey brain matter. Applicant made this discovery using a two-needle probe to contact portions of fresh frozen rabbit brains thawed to room temperature. The rabbit brains contained edematous regions caused by the previous implantation of a rabbit brain tumor. The two-needle probe was connected to an impedance meter for a display of the local impedance value. Impedance measurements were performed with the insertion of a probe needle into normal and edematous white and grey matter as the frozen brains thawed from 4° to 22° C. As shown, in FIG. 1, the edematous grey and edematous white conductivity values were higher than normal tissue. Applicant believes that the higher conductivity in the edematous tissue is because the tissue becomes diffused or prefused with high conductivity edematous fluid. Similar results were obtained at frequencies from one to four megahertz.

FIG. 2 is a schematic representation of a generalized embodiment of the present invention. A drive/sensor coil 10 produces an alternating magnetic field 12. Although the magnetic field intensity lines pass through the brain, the magnetic field intensity lines are more highly concentrated in the plane of the drive/sensor coil 10. The alternating magnetic field (12) generate an electrical field 14 which induces eddy currents in brain tissue and fluid. One such eddy current is graphically represented by element 16 on FIG. 2. The magnitude of the eddy current is proportional to the magnitude of the electric field 14 multiplied by the conductivity of brain tissue and fluid that particular eddy current travels though (i.e., magnitude of eddy current is proportional to $E \times \sigma$ where E is the magnitude of the electric field and $\sigma$ is conductivity). The eddy current alternates in accordance with the alternating magnetic field 12. The alternating eddy current 16 generates a second weaker magnetic field 18. This magnetic field 18 induces a corresponding E field on the sense coil 10 which is detected and processed by the appropriate circuitry.

The sense coil 10 actually detects the secondary magnetic field 18 generated from a multitude of such tiny eddy currents induced in the brain tissue and fluid excited by the primary magnetic field 12. Since we are interested in localized impedance measurements, spatial and temporal techniques are used to either reduce the area of brain excitation by the primary magnetic field 12 or temporally separating the reception of secondary magnetic field 18 from a selected area of the brain. In the generalized embodiment shown in FIG. 2, the drive/sensor loop coil 10 produces some degree of localization by intensifying the magnetic field in the plane of the coil 10.

FIG. 3 is a schematic representation of a non-invasive apparatus to measure localized brain impedance as taught by the present invention. The drive/sensor coil is a thin or narrow magnetic field coil winding 20. Oscillator/Detector 22 provides an alternating electric current in coil 20 which produces an alternating magnetic field. If tissue becomes edematous in the brain (in an area of thrombosis, for example) within the proximity of coil 20, the mutual inductance of the coil changes the frequency of oscillation of the oscillator/detector 22. The magnitude of the frequency change is proportional to the value of the electrical conductivity located within the drive/sensor coil 20. In summary, the magnetic field produced by the drive/sensor coil 20 creates an electric field. The electric field creates induced eddy currents within the brain tissue and fluid. These induced eddy currents re-radiate a secondary magnetic field, which is detected by the drive/sensor coil 20 and in effect changes its mutual inductance. The change in mutual inductance of the coil causes the oscillator frequency of the oscillator/detector 22 to correspondingly change.

Returning to FIG. 3, a portion of a patient's head would be placed through detector coil 20 which non-invasively ascertains the electrical conductivity in that section of the brain. Oscillator/detector 22 is connected to the coil 20 and generates an oscillating magnetic signal in the coil. The change in mutual inductance of the coil is picked up by oscillator/detector 22 and results in a change in output 24 indicating a frequency change and in output 26 indicating a voltage change. The magnitude of electrical conductivity (or impedance) of a particular section of the brain is thus detected. In this embodiment the drive/sensor coil 20 would be placed around an area of interest (such as a trauma site) and the time history of that area would be monitored.

FIG. 4 is a schematic drawing of one possible circuit configuration for oscillator/detector 22. Electronically, the circuit represents a marginally stable Colpitts oscillator whose frequency of oscillation is determined by the tank circuit. Although a Hartley-type oscillator, or similar, would work equally well. The potentiometer tap 30 helps to find the proper circuit resistance external to the tank circuit 32 resistance that is needed for stable oscillation. The tank circuit 32 includes coil 20 and capacitors 34. The amplifier 36 with negative feedback provides stable voltage gain. A DC output 24 is extracted from the demodulator diode 38 which reflects the change in oscillator amplitude. The frequency is measured directly off coil 20 at output 26. When a patient's head is placed through coil 20, eddy currents are induced by the time changing magnetic field generated by drive/sensor coil 20. The eddy currents in turn produce a secondary, though slight, magnetic field whose associated field is coupled back to the drive/sensor coil 20. This produces a change in the coil impedance which changes the resonant amplitude, measured at output 24, and the resonant frequency, measured at output 26, of tank circuit 32. The coil inductances are in the millihenry (mH) range so that resonant frequencies in the hundreds of kHz to several MHz are obtained. In this frequency range, the impedance changes are dominated by conductivity properties and not polarization effects caused by the relative permittivity of the media.

Figure 5:
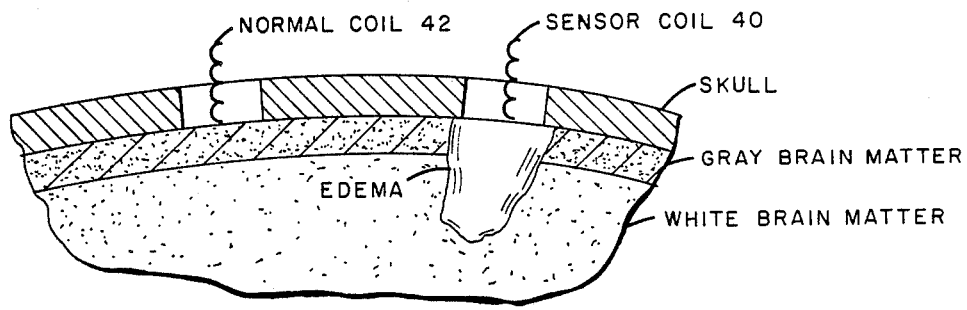
FIG. 5 is an illustration of the experimental configuration used to study time-trend data during the formation of edematous tissue.
Figure 6:
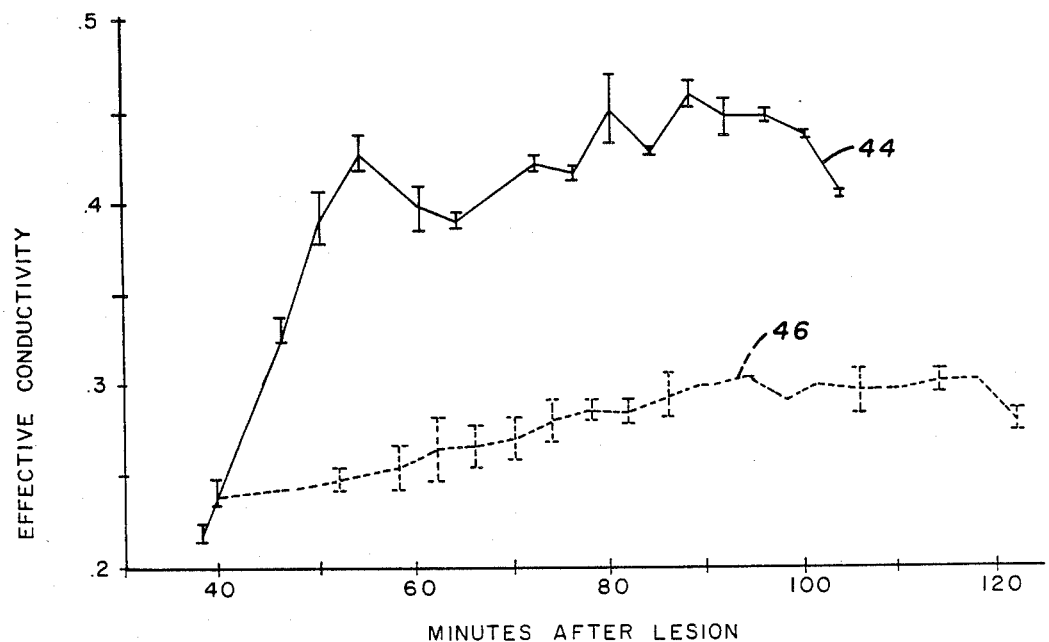
FIG. 6 is a graphic representation of the conductivity changes over time measured by the present invention showing development of edematous tissue.

FIG. 5 shows an actual experimental configuration used by the Applicant to detect the time-trends of edema in an animal brain. A first sensor coil 40 was placed over a cold lesion used to induce edema in the brain. A second sensor coil 42 was placed over a normal region in the same animal where no lesion was produced. (Note: Optional bore holes were cut in the skull so that a cold lesion could be made at one location. However, the bore holes were not necessary to take measurements.) Coils 40 and 42 are solenoid type coils that were connected to the circuit generally shown in FIG. 4. These coils sensed the conductivity of brain matter in a region below each coil and extending a distance toward the center of the brain. FIG. 6 is a graph showing the experimental results. Graph 44 shows the general results measured from the sensor coil 40 over the edematous region and graph 46 shows the results measured from the sensor placed over the normal tissue. As time progresses, there is obviously a measurable change in graph 44 caused by both a conductivity change in the edematous white brain matter and a growth of the edematous volume. It will also be noted that graph 46 shows a slight increase in conductivity over time. This is believed due to the slight formation of edema caused by exposure of the brain's dura to the air.

Figure 7:
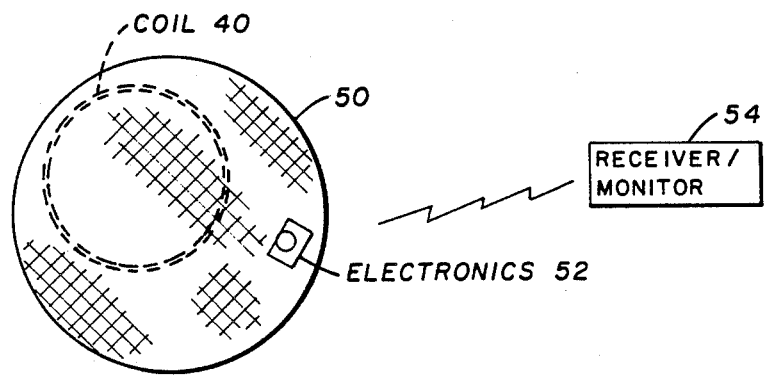
FIG. 7 is a block diagrammatic illustration of the present invention showing the coil and electronics mounted on a gauze pad.

FIG. 7 is an embodiment of the invention useful in he clinical setting. A flexible coil sensor 48 is packaged in a flexible gauze-like material 50 and stuck to the patient's head over a spot where a physiological change is expected. For example, the flexible coil sensor might be placed over a local head injury that might be complicated with the onset of brain edema. The coil, which could be made with various dimensions (for example, ½, 1, 2 inches), is connected to chip electronics 52, powered by a small battery. The chip electronics 52 could contain a transmitter that telemeters the information signal to a monitor 54. Alternatively, the information signal could be sent along wires to the monitor.

Figure 8:
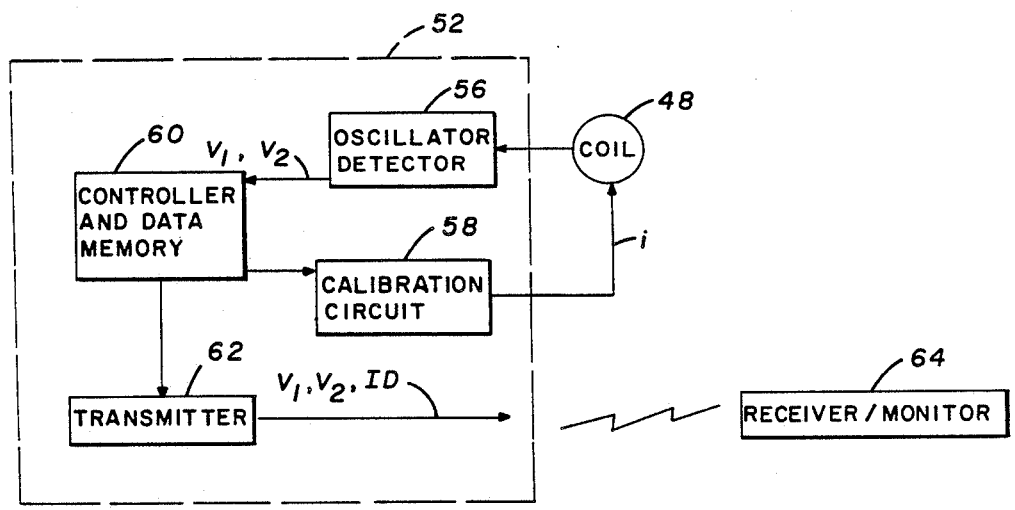
FIG. 8 is a block diagram of the processing electronics used in the present invention to measure time-trends at a particular region of the brain.

FIG. 8 is a block diagram showing the system configuration of the coil 48 and chip electronics 52. Oscillator detector 56 (similar in design to the circuit shown in FIG. 4) is operably connected to coil 48 and senses the conductivity in the brain matter. A calibration circuit 58 periodically, from command by a controller circuit 60, sends a calibration current to coil 48 which senses the calibration current with the oscillator detector 56. An alternative calibration method would be to send the calibration current to a separate coil, wound within coil 48, this second coil used only to generate a calibration signal for coil 48 to sense. Both the physiological signal output ($V_1$) and the calibration signal output ($V_2$) are stored in controller 60. These voltage values are transmitted by an RF transmitter 62, or by wire, to a remote monitor station 64, where the signal output voltage value ($V_1$) is corrected for drift or background noise with the calibration voltage value ($V_2$). The monitor contains a programmed micro-computer that can equate the resultant conductivity change with a physiological abnormality by the extend and rate-of-change of the conductivity shift. The transmitter 62 could also emit an identification (ID) to tag each patient. The coil 48, oscillator detector 56, calibration circuit 58, controller 60 and optional RF transmitter 62 could be packaged on the expendable gauze-like substrate.

In operation the device of FIG. 7 and 8 would be placed over the spot where physiological changes are expected. (For example, over the site of a local head injury.) The system would take periodic measurements (with periodic calibration measurements) and provide via monitor 64 an output showing conductivity time-trends. An increase of conductivity with time, would be indicative of an edematous condition.

Obviously many modifications and variations of the present invention are possible in light of the above teachings. It is, therefore, to be understood that within the scope of the appended claims, the invention may be practiced otherwise than is specifically described.

What is claimed is:

1. An apparatus for sensing physiological changes in an animal or human brain, comprising:
   a coil adapted to generate a magnetic field in a selected portion of a patient's brain;
   a pad which is adapted to be placed on a patient's head over a selected localized site, wherein said coil is mounted in said pad;
   an oscillator/detector means for exciting said coil with a time-varying electrical signal, for detecting changes in mutual inductance of said coil, and for outputting an information signal corresponding to such detected changes in mutual inductance, wherein changes in mutual inductance are caused by a secondary induced magnetic field which varies in response to the impedance of brain matter and fluid located in said selected portion of the patient's brain;
   a calibration means for exciting said coil with a calibration current having a set value;
   a controller and data memory means for periodically actuating said calibration means and for storing values for said information signal, wherein calibration data is stored when said calibration means is actuated, and measurement data is stored when said calibration means is off;
   a means for correcting said measurement data for drift and background noise based on calibration data; and, a display means for displaying corrected measurement data.

2. The apparatus of claim 1, wherein said oscillator/detector means is mounted in said pad.

3. The apparatus of claim 1, wherein said calibration means is mounted in said pad.

4. The apparatus of claim 1, wherein said oscillator/detector means, calibration means and controller and data memory means are mounted in said pad which is adapted to be placed on a patient's head over the site of a head injury.

5. The apparatus of claim 4, further comprising:
   a transmitter operably coupled to said controller and data memory means for transmitting a signal containing said calibration data and said measurement data; and,
   a receiver means operably coupled to said correction means for receiving said transmitted signal containing calibration data and measurement data.

6. The apparatus of claim 5, wherein said transmitter is mounted in said pad.

7. A method of monitoring head injury for occurrence of edema, comprising the step of:
   directing a spatially concentrated magnetic field into the patient's brain at the area of interest, whereby currents induced in brain matter and fluid located in said area of interest will produce a secondary magnetic field which varies in response the impedance of brain matter and fluid located in said area of interest; and,
   detecting the magnitude of said secondary magnetic field, wherein the magnitude of said secondary magnetic field is indicative of the conductivity of brain matter and fluid located in said area of interest.

8. The method of claim 7, further comprising the steps of comparing changes in the detected magnitude of said secondary magnetic field over time to monitor time-trends, wherein increase in conductivity over time is indicative of edematous tissue forming in said brain at said area of interest.

9. The method of claim 7, further comprising the steps of periodically calibrating the electrical circuit used to generate said spatially concentrated magnetic field and correcting the magnitude of said secondary magnetic field to correct for drift or background noise based on calibration data.

* * * * *